(12) United States Patent
Predick et al.

(10) Patent No.: US 10,178,987 B2
(45) Date of Patent: Jan. 15, 2019

(54) RETRACTOR

(71) Applicant: Life Spine, Inc., Huntley, IL (US)

(72) Inventors: Daniel Predick, Chicago, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 102 days.

(21) Appl. No.: 14/874,073

(22) Filed: Oct. 2, 2015

(65) Prior Publication Data
US 2016/0051242 A1 Feb. 25, 2016

Related U.S. Application Data

(63) Continuation-in-part of application No. 13/720,800, filed on Dec. 19, 2012, now Pat. No. 9,386,916.

(60) Provisional application No. 61/577,857, filed on Dec. 20, 2011.

(51) Int. Cl.
*A61B 17/02* (2006.01)

(52) U.S. Cl.
CPC .................. *A61B 17/0206* (2013.01)

(58) Field of Classification Search
CPC .................................. A61B 17/0293
See application file for complete search history.

(56) References Cited

U.S. PATENT DOCUMENTS

| | | | |
|---|---|---|---|
| 530,728 A * | 12/1894 | Sherbrook | A61B 1/32 600/224 |
| 3,509,873 A | 5/1970 | Karlin | |
| 4,065,941 A | 1/1978 | Aoki | |
| 7,335,207 B1 | 2/2008 | Smith | |
| 2004/0049101 A1 | 3/2004 | Phillips et al. | |
| 2005/0215866 A1 | 9/2005 | Kim | |
| 2007/0049930 A1 | 3/2007 | Hearn et al. | |
| 2007/0203399 A1* | 8/2007 | Gephart | A61B 1/32 600/219 |
| 2007/0238932 A1 | 10/2007 | Jones et al. | |
| 2010/0154604 A1 | 6/2010 | Su | |
| 2010/0222644 A1* | 9/2010 | Sebastian | A61B 17/0206 600/228 |
| 2011/0130793 A1* | 6/2011 | Woolley | A61B 17/0206 606/279 |
| 2011/0301423 A1 | 12/2011 | Koros et al. | |
| 2014/0024900 A1 | 1/2014 | Capote et al. | |
| 2015/0230787 A1 | 8/2015 | Friedrich et al. | |
| 2015/0250467 A1* | 9/2015 | Higgins | A61B 17/0206 600/215 |

(Continued)

FOREIGN PATENT DOCUMENTS

| | | | | |
|---|---|---|---|---|
| WO | WO 2015/134367 A1 | 9/2015 | | |
| WO | WO 2015/160343 | * 10/2015 | ............. | A61B 17/02 |
| WO | WO 2015160343 | * 10/2015 | ............. | A61B 17/02 |

*Primary Examiner* — Samuel Hanna
(74) *Attorney, Agent, or Firm* — Foley & Lardner LLP

(57) ABSTRACT

A retractor assembly includes a base; a first side arm assembly coupled to a first side of the base and configured to translate relative to the base along a first direction; a second side arm assembly coupled to a second side of the base and configured to translate relative to the base along the first direction independent from the first side arm assembly; and a central arm assembly coupled to a center portion of the base and configured to translate relative to the base along a second direction different from the first direction.

9 Claims, 16 Drawing Sheets

(56) References Cited

U.S. PATENT DOCUMENTS

2015/0305731 A1 10/2015 Friedrich et al.
2015/0313585 A1 11/2015 Abidin et al.

\* cited by examiner

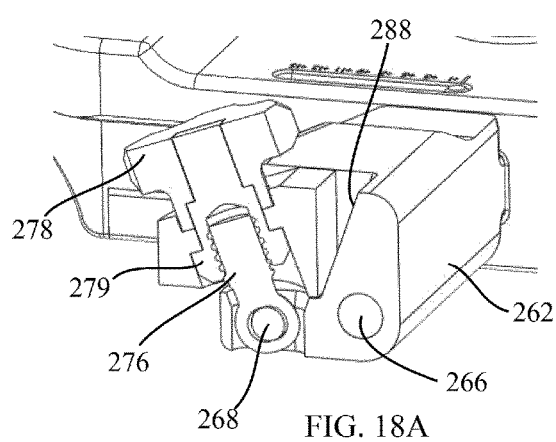
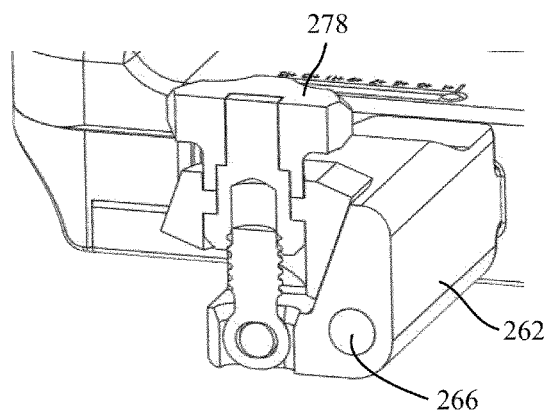
FIG. 18A
FIG. 19A
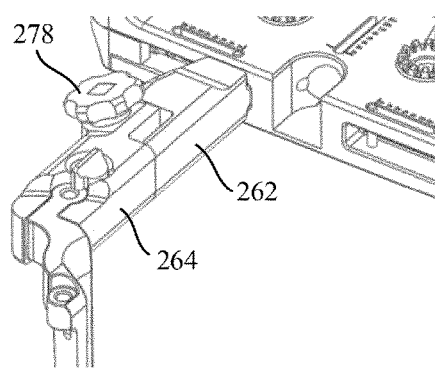
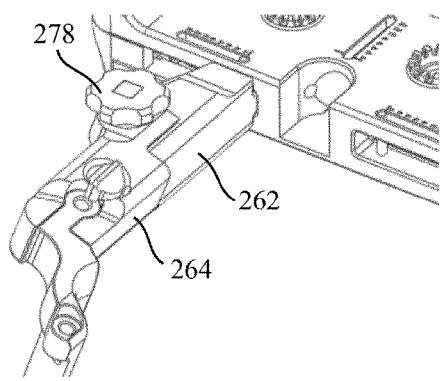
FIG. 18B
FIG. 19B

RETRACTOR

CROSS-REFERENCE TO RELATED PATENT APPLICATIONS

This application is a continuation-in-part of U.S. patent application Ser. No. 13/720,800, filed Dec. 19, 2012, which claims the benefit of U.S. Provisional Patent Application No. 61/577,857 filed Dec. 20, 2011. The entire contents of both of these applications are incorporated herein by reference.

BACKGROUND

The present invention relates to surgical devices for retracting anatomy to provide exposure of an operating site, and more particularly, to refraction apparatus providing improved access to a surgical site for a spine procedure.

Surgical procedures typically require the use of a retractor to hold anatomies and/or tissues out of the way from the incision down to the actual surgical site. In the case of posterior spinal surgery for implanting various spine fixation components and/or other spinal orthopedic devices, it is necessary to retract different tissue types including large and strong paraspinal muscles in order to get to the actual surgical site. In order to accomplish this goal, spinal retractors have been developed that hold back the desired anatomy of a spinal surgical site and is fixed relative to the patient either directly or indirectly.

Many different types of spinal retractors are currently available many of which use retractor blades—a part of the distraction mechanism of the spinal refractor that enters the site of the incision and physically holds the anatomy apart. The retractor blades can be attached to a frame at an angle such as about 90 degrees from horizontal (i.e. generally vertical) or as to have a variable angle. However, current spinal retractors have various deficiencies. For instance, fixed angle retractor blade configurations limit flexibility of the spinal retractor, including loss of surgical site precision and overall stabilization. The variable angle retractor blade configurations lack preciseness and flexibility in retractor blade positioning.

It is therefore evident from the above that there is a need for an improved spinal retractor that can overcome the deficiencies of current spinal retractors. It is also evident from the above that there is a need for an improved spinal retractor which provides enhanced preciseness and flexibility in retractor blade positioning. It is furthermore evident that there is a need for an improved spinal retractor as aforementioned which also allows for instrument and/or component retention and positioning by the retractor blade assembly.

SUMMARY

The present invention is a spinal retractor for spinal surgeries providing improved preciseness and stability in positioning, tissue distraction, and surgical site access. The spinal retractor utilizes adjustable and lockable translating arms with angulating blades to provide a stable surgical site finestra and the adjustable retraction of surgical site tissue.

The present spinal retractor is a three blade retractor that allows triangulated medial/lateral and cephalad/caudal tissue retraction for spinal surgeries via the adjustably lockable translating arms. A medial/lateral translating arm with an angularly adjustable retraction blade co-acts and cooperates with angularly adjacent first and second cephalad/caudal translating arms with angularly adjustable refraction blades for tissue retraction and surgical site access.

The spinal retractor includes a plate having a medial/lateral adjustment system adjustably holding the medial/lateral translating arm, a first cephalad/caudal adjustment system adjustably holding the first cephalad/caudal translating arm, and a second cephalad/caudal adjustment system adjustably holding the second cephalad/caudal translating arm. The translating arms each have a blade holder which provides angular adjustment of the blade. Angular adjustment of each blade along with medial/lateral and cephalad/caudal adjustment provides improved preciseness and stability in positioning, tissue distraction, and surgical site access.

Further aspects of the present invention will become apparent from consideration of the drawings and the following description of a preferred embodiment of the invention. A person skilled in the art will realize that other embodiments of the invention are possible and that the details of the invention can be modified in a number of respects without departing from the inventive concept. The following drawings and description are to be regarded as illustrative in nature and not restrictive.

Another embodiment relates to a retractor assembly, comprising a base; a first side arm assembly coupled to a first side of the base and configured to translate relative to the base along a first direction; a second side arm assembly coupled to a second side of the base and configured to translate relative to the base along the first direction independent from the first side arm assembly; and a central arm assembly coupled to a center portion of the base and configured to translate relative to the base along a second direction different from the first direction.

Another embodiment relates to a retractor assembly, comprising a base; a first side arm assembly coupled to a first side of the base and configured to translate relative to the base along a first direction; a second side arm assembly coupled to a second side of the base and configured to translate relative to the base along the first direction; and a central arm assembly coupled to a center portion of the base and configured to translate relative to the base along a second direction different from the first direction; wherein each of the first side arm assembly, the second side arm assembly, and the center arm assembly is coupled to the base by an adjustment mechanism including a bevel gear drive.

Another embodiment relates to a method of operating a retractor, comprising placing a retractor into a desired position, wherein the retractor includes a frame, a first side assembly, a second side assembly, and a center assembly; translating the first side assembly relative to the frame along a first threaded shaft and independent from the second side assembly and the center assembly; translating the second side assembly relative to the frame along a second threaded shaft and independent from the first side assembly and the center assembly; and translating the center assembly relative to the frame along a third threaded shaft and independent from the first side assembly and the second side assembly.

BRIEF DESCRIPTION OF THE DRAWINGS

The features of the invention will be better understood by reference to the accompanying drawings which illustrate a presently preferred embodiment of the invention, wherein:

FIGS. 18A-19B illustrate various portions of a spinal retractor according to one embodiment.

Like reference numbers indicate the same or similar parts throughout the several figures.

Figure 1:
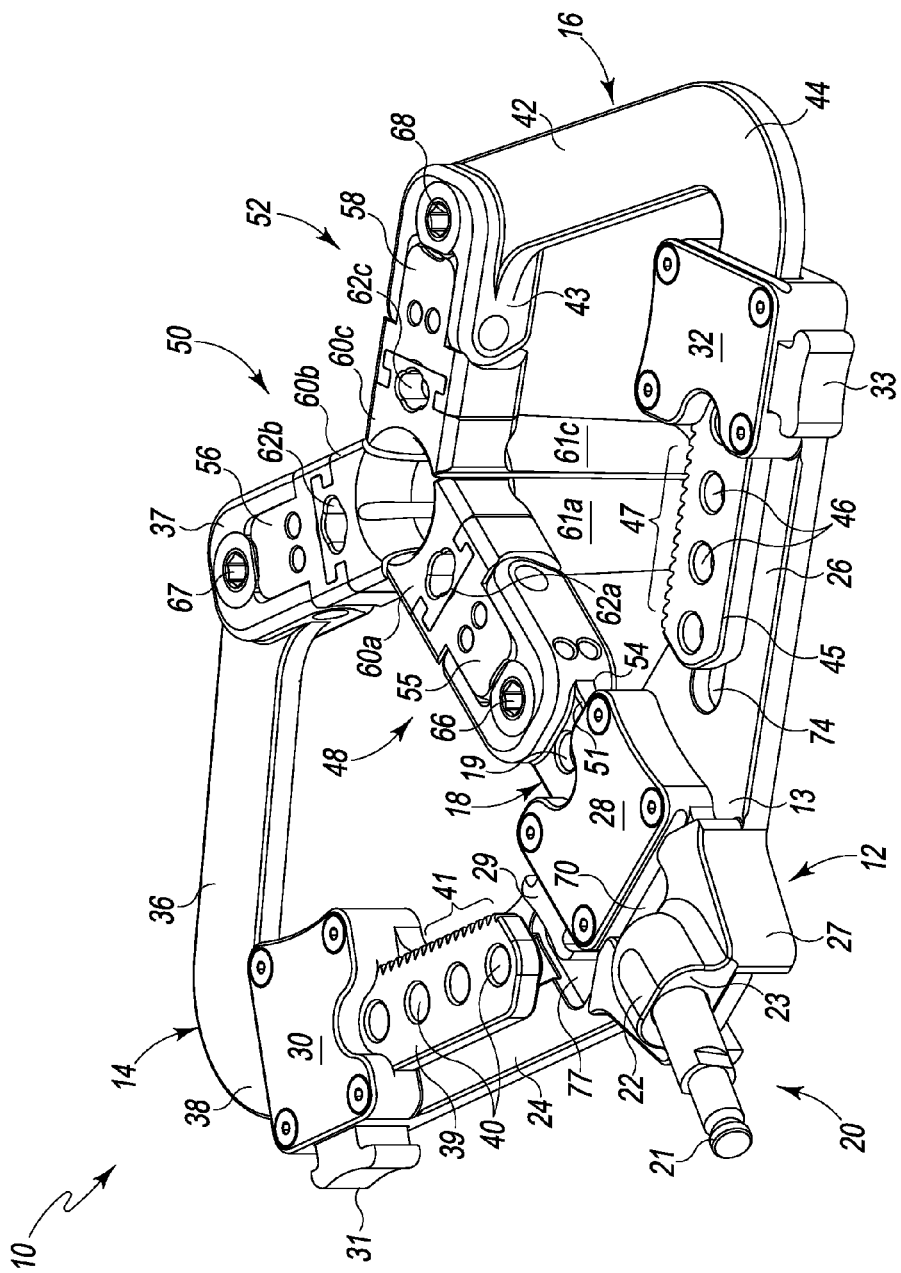
FIG. 1 is a topside view of a spinal retractor fashioned in accordance with the present principles, the spinal retractor shown in a closed position.

A description of the features, functions and/or configurations of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Reference is now made to FIGS. 1-5 which depict several views of a spinal retractor 10, fashioned in accordance with the present principles. The spinal retractor 10 is fashioned for use in anterior, posterior and lateral spinal surgeries or procedures, such as orthopedic implantation, vertebral fixation and vertebral stabilization, but may be used in other surgical procedures and orientations. The spinal retractor 10 is formed of an appropriate surgical material such as titanium, stainless steel, an alloy of same or the like.

The spinal retractor 10 has a body 12 characterized by a base, plate, platform or the like 13, a first translating arm 14 carried by the base 13 on one side thereof, a second translating arm 16 carried by the base 13 on another side thereof, wherein the sides are in the cephalad/caudal direction when the spinal retractor 10 is used, and a middle arm 18 carried by the base between the first and second trans- lating arms 14, 16, wherein the middle arm is in the lateral/medial direction when the spinal retractor 10 is used. The base 13 further has a first side arm or wing 24 extending from a first side of the base 13 and a second side arm or wing 26 extending from a second side of the base 13. The first and second side arms 24, 26 extend generally in opposite directions relative to each other but with a slight inward angle as shown. The first and second side arms 24, 26 are in the cephalad/caudal direction when the spinal retractor 10 is used.

The spinal retractor 10 is designed to be fixed relative to a surgical site particularly, but not necessarily, to an external frame or the like (not shown) that is fixed relative to the patient. The spinal retractor 10 is also configured for rotation relative to the external frame. As such the base 13 has a boss 22 situated between opposite edges 25, 27, the boss 22 defining a face 23 from which projects a post, shaft, pole, bar, rod, stick or the like (i.e. a projection) 21. The spinal retractor 10 is connected with the external frame via the projection 21 which is received in or by a clamp, holder, receiver or the like (not shown) of the external frame. The projection 21 has a textured or keyed outer surface for engagement with the external frame, shown in the figures as radially spaced longitudinal grooves. The external surface of the projection 21 aids in positive engagement of the spinal retractor 10 with the external frame in order to fix rotational position of the spinal retractor 10 relative to the external frame.

A housing 28 is disposed on the base 13 between the first and second side arms 24, 26 and has an opening that receives the arm 18. The housing 28 cooperates with the arm 18 to provide adjustment of the arm 18 relative to the housing 28. Particularly, the arm 18 has a plurality of teeth, serrations or the like 51 on an inside edge thereof while the housing 28 includes ratchet components that cooperate with the teeth 51 of the arm 18 to provide ratcheting adjustability/translation of the arm 18 relative to the base 13. A button 29 is associated with the housing 28 and is coupled to the internal ratchet components thereof in order to allow release of the ratcheted (fixed) position of the arm 18 relative to the housing 28. In this manner, the arm 18 translates or slides in and out relative to the housing 28/base 13. Additionally, since a blade assembly 48, as described more fully below, is connected to the arm 18, the blade assembly 48 translates relative to the housing 28/base 13. This allows the blade assembly 48 to be positioned relative to the housing 28/base 13 and to the other blade assemblies 50, 52. Because of its position, the arm 18 and thus the blade assembly 48 translate or move in the medial/lateral directions when the spinal retractor 10 is in use. Position of the blade assembly 48 affects and effects retraction of tissue at the surgical site, particularly in the medial/lateral directions.

A housing 30 is disposed on an end of the first side arm 24 and has an opening that receives the first translating arm 14. The housing 30 cooperates with the first translating arm 14 to provide adjustment of the first translating arm 14 relative to the housing 30. Particularly, the first translating arm 14 has a plurality of teeth, serrations or the like 41 on an inside edge of an end 39 of the first translating arm 14 while the housing 30 includes ratchet components that cooperate with the teeth 41 of the first translating arm 14 to provide ratcheting adjustability/translation of the first translating arm 14 relative to the first side arm 24/base 13. A button 31 is associated with the housing 30 and is coupled to the internal ratchet components thereof in order to allow release of the ratcheted (fixed) position of the first translating arm 14 relative to the housing 30. In this manner, the first translating arm 14 translates or slides in and out relative to the housing 30/first side arm 24. Additionally, since the blade assembly 50, as described more fully below, is connected to the first translating arm 14, the blade assembly 50 translates relative to the housing 30/first side arm 24. This allows the blade assembly 50 to be positioned relative to the housing 30/first side arm 24 and to the other blade assemblies 48, 52.

Mention is now made to the configuration of the first translating arm 14. The first translating arm 14 is angled or bent so as to define a "boomerang" shape—i.e. an elbow or bend 38 between arm segments 36 and 39. Particularly, arm segments 36, 39 are bent to have an internal angle of less than ninety degrees (angle <90°) with around seventy degrees (70°) being shown and preferred. Other angles, of course, may be used. A head 37 is provided at an end of the arm segment 36 opposite the bend 38 and is angled so as to project essentially parallel with the arm segment 39. The head 37 holds the blade assembly 50. As seen, the first translating arm 14 is angled so that its blade assembly 50 is proximate the blade assembly 48 of the arm 18.

The first translating arm 14 moves in and out relative to the housing 30 and thus the first side arm 24 through ratcheting of the arm segment 39 with its plurality of teeth 41 cooperating with the ratchet components of the housing 30. Movement of the arm 14 moves the corresponding blade assembly 50 relative to the other blade assemblies 48, 52. Because of its position and connection with the housing 30, the first translating arm 14 translates or moves in the cephalad/caudal directions so that the blade assembly 50 also moves in the cephalad/caudal directions. Position of the blade assembly 50 affects and effects retraction of tissue at the surgical site, particularly in the cephalad/caudal directions.

A housing 32 is disposed on an end of the second side arm 26 and has an opening that receives the second translating arm 16. The housing 32 cooperates with the second translating arm 16 to provide adjustment of the second translating arm 16 relative to the housing 32. Particularly, the second translating arm 16 has a plurality of teeth, serrations or the like 47 on an inside edge of an end 45 of the second translating arm 16 while the housing 32 includes ratchet components that cooperate with the teeth 47 of the second translating arm 16 to provide ratcheting adjustability/translation of the second translating arm 16 relative to the second side arm 26/base 13. A button 32 is associated with the housing 32 and is coupled to the internal ratchet components thereof in order to allow release of the ratcheted (fixed) position of the second translating arm 16 relative to the housing 32. In this manner, the second translating arm 16 translates or slides in and out relative to the housing 32/second side arm 26. Additionally, since the blade assembly 52, as described more fully below, is connected to the second translating arm 16, the blade assembly 52 translates relative to the housing 32/second side arm 26. This allows the blade assembly 52 to be positioned relative to the housing 32/second side arm 26 and to the other blade assemblies 48, 50.

Mention is now made to the configuration of the second translating arm 16. The second translating arm 16 is angled or bent so as to define a "boomerang" shape—i.e. an elbow or bend 44 between arm segments 42 and 45. Particularly, arm segments 42, 45 are bent to have an internal angle of less than ninety degrees (angle <90°) with around seventy degrees (70°) being shown and preferred. Other angles, of course, may be used. A head 43 is provided at an end of the arm segment 42 opposite the bend 44 and is angled so as to project essentially parallel with the arm segment 45. The head 43 holds the blade assembly 52. As seen, the second translating arm 16 is angled so that its blade assembly 52 is proximate the blade assembly 48 of the arm 18.

The second translating arm 16 moves in and out relative to the housing 32 and thus the second side arm 26 through ratcheting of the arm segment 45 with its plurality of teeth 47 cooperating with the ratchet components of the housing 32. Movement of the arm 16 moves the corresponding blade assembly 52 relative to the other blade assemblies 48, 50. Because of its position and connection with the housing 32, the second translating arm 16 translates or moves in the cephalad/caudal directions so that the blade assembly 52 also moves in the cephalad/caudal directions. Position of the blade assembly 52 affects and effects retraction of tissue at the surgical site, particularly in the cephalad/caudal directions.

Ratcheting adjustment of the arm 18 and of the first and second translating arms 14, 16 (and thus adjustment of the blade assemblies 48, 50, 52) may be accomplished manually but are preferably adjusted via one or more surgical instruments or tools. As such, the arms 18, 24, 26 and the base 13 are configured to allow manipulation of the arms 18, 24, 26 by a surgical instrument or tool (not shown).

Figure 4:
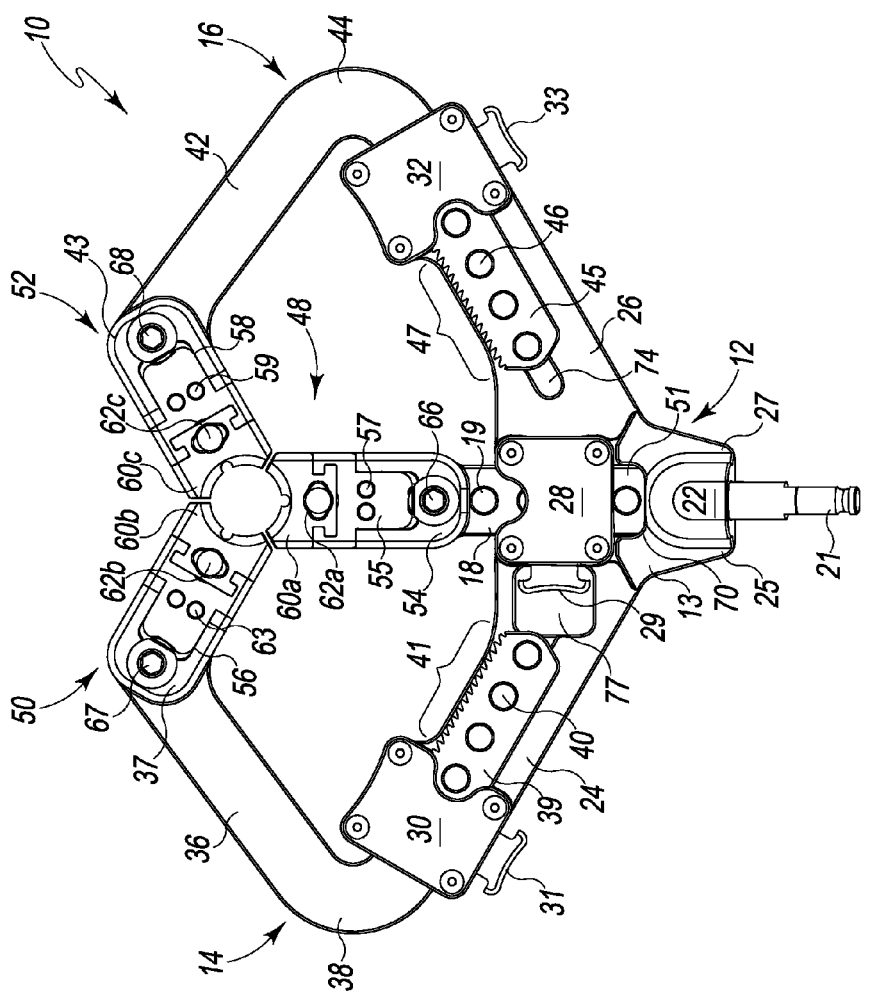
FIG. 4 is a top plan view of the spinal retractor of FIG. 1 in a closed position.

As best seen in FIGS. 1 and 4, the arm 18 has a series of holes 19 that extend along its longitudinal length. The base 13 has a slot 70 that extends through the housing 28 and which is sized to receive the arm 18. The arm 18 thus translates within the slot 70. One or more holes 19 of the arm 18 accepts a surgical instrument, tool and/or instrument/tool portion to manually move the arm 18 within the slot 70 and in conjunction/cooperation with the ratcheting housing 28. As should be appreciated, the ratcheting housing 28 allows incremental locking movement of the arm 18 in one direction while prohibiting movement in an opposite direction without the release thereof. In the case of arm 18, the arm 18 incrementally locks in a direction toward the base 13 in order to hold tissue by the blade assembly 48 in the medial/lateral direction. This allows the surgeon to incrementally manipulate the blade assembly 48 and thus the amount of tissue retraction by the blade assembly 48. Release is accomplished by the button/ratchet release system 29 associated with the housing/ratchet system 28. As best seen in FIG. 4, the button 29 extends from the housing 28 into a configured notch or recess 77 in the first side arm 24. Recessing the button 29 helps to prevent accidental activation and thus release of tissue retraction.

Figure 3:
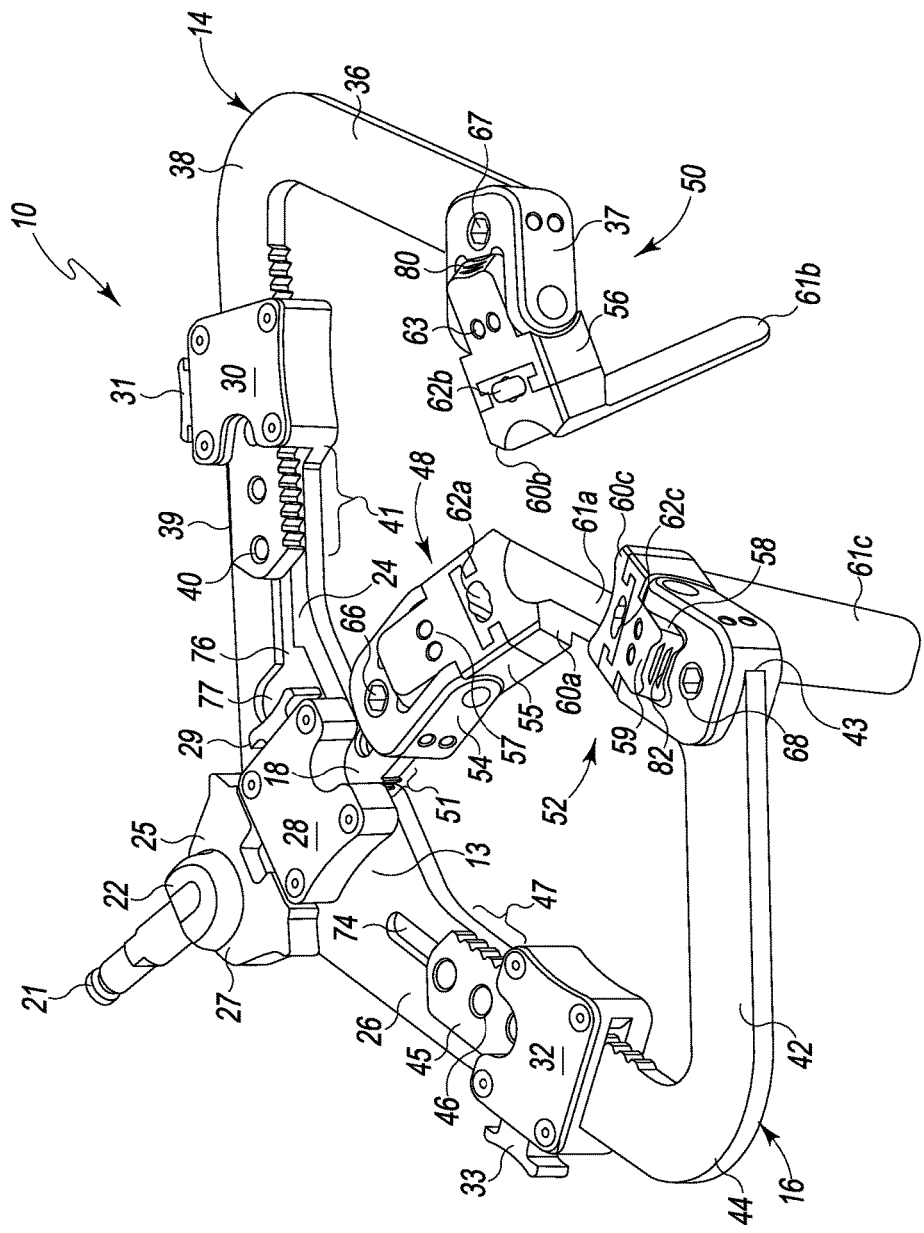
FIG. 3 is another topside view of the spinal retractor of FIG. 1 in an open position.

As best seen in FIGS. 1, 3 and 4, the first translating arm 14 has a series of holes 40 that extend along a length of the end segment 39. In conjunction therewith, the first side arm 24 of the base 13 has a slot 76 that extends from the configured recess 77 into the housing 30. The slot 76 is sized both in width and length to fit under the arm segment 39 and particularly under the holes 40. One or more holes 40 of the first translating arm 14 accepts a surgical instrument, tool and/or instrument/tool portion to manually move the arm 14 over the slot 76 and in conjunction/cooperation with the ratcheting housing 30. As should be appreciated, the ratcheting housing 30 allows incremental locking movement of the arm 14 in one direction while prohibiting movement in an opposite direction without the release thereof. In the case of the first translating arm 14, the arm 14 incrementally locks in a direction along the longitudinal length of the first side arm 24 inwardly toward the base 13 in order to hold tissue by the blade assembly 50 in the cephalad/caudal direction. This allows the surgeon to incrementally manipulate the blade assembly 50 and thus the amount of tissue retraction by the blade assembly 50. Release is accomplished by the button/ratchet release system 31 associated with the housing/ratchet system 30. The button 31 extends outward from the housing 30 helping to prevent accidental activation and thus release of tissue retraction.

As best seen in FIGS. 1, 3 and 4, the second translating arm 16 has a series of holes 46 that extend along a length of the end segment 45. In conjunction therewith, the second side arm 26 of the base 13 has a slot 74 that extends from proximate an end of the second side arm 26 near the base 13 and into the housing 32. The slot 74 is sized both in width and length to fit under the arm segment 45 and particularly under the holes 46. One or more holes 46 of the second translating arm 16 accepts a surgical instrument, tool and/or instrument/tool portion to manually move the arm 16 over the slot 74 and in conjunction/cooperation with the ratcheting housing 32. As should be appreciated, the ratcheting housing 32 allows incremental locking movement of the arm 16 in one direction while prohibiting movement in an opposite direction without the release thereof. In the case of the second translating arm 16, the arm 16 incrementally locks in a direction along the longitudinal length of the second side arm 26 inwardly toward the base 13 in order to hold tissue by the blade assembly 52 in the cephalad/caudal direction. This allows the surgeon to incrementally manipulate the blade assembly 52 and thus the amount of tissue retraction by the blade assembly 52. Release is accomplished by the button/ratchet release system 33 associated with the housing/ratchet system 32. The button 33 extends outward from the housing 32 helping to prevent accidental activation and thus release of tissue retraction.

Figure 2:
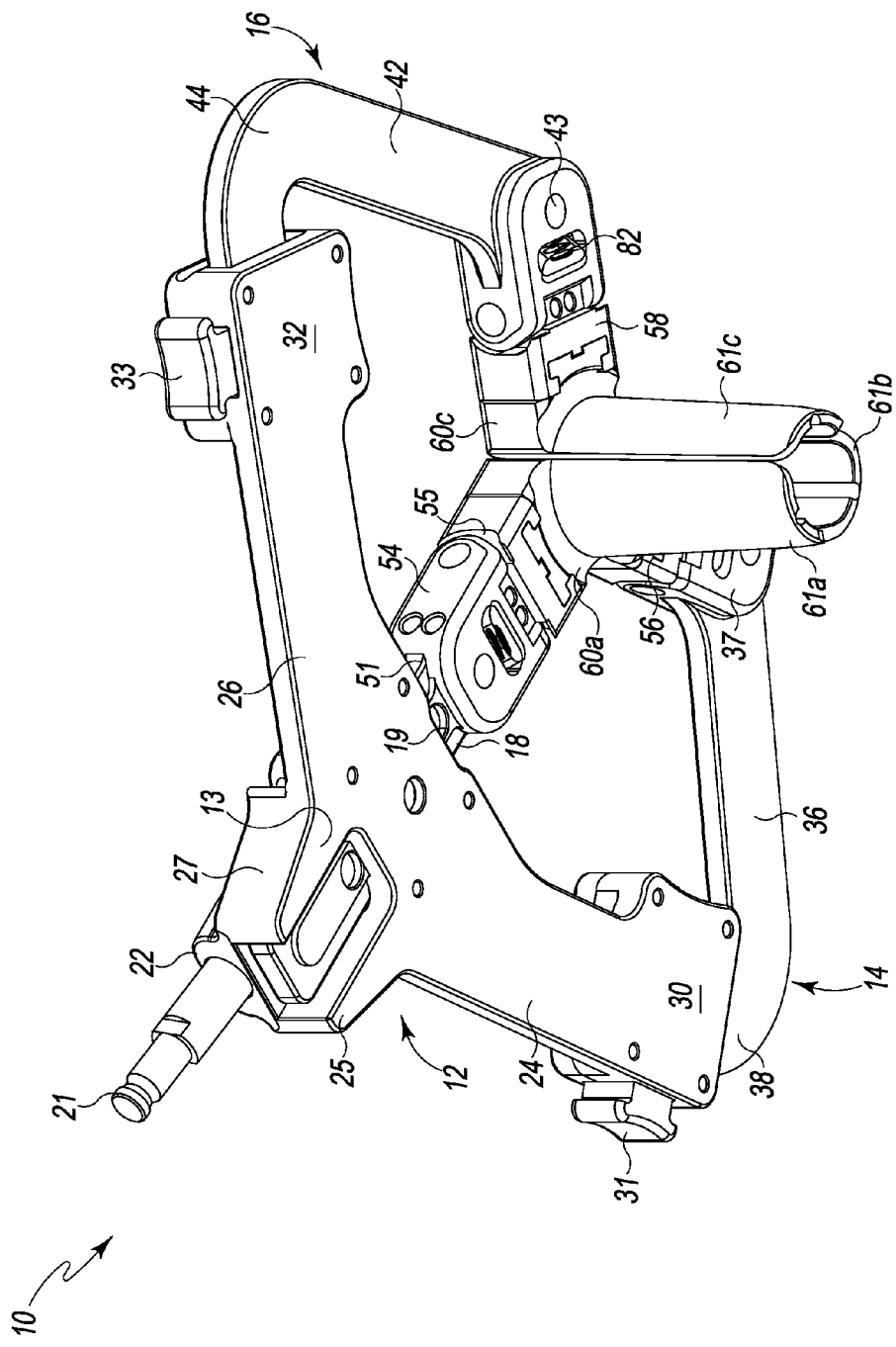
FIG. 2 is an underside view of the spinal retractor of FIG. 1 shown in a closed position.

As seen in the figures each arm 18, 14 and 16 has a respective blade assembly 48, 50, 52 for holding and retracting tissue during spinal surgery. The blade assembly 48 includes a head 54 which pivotally retains a blade holder 57 via an angulation system controlled by a set screw 66, the head 54 holding a blade 60*a*. The blade assembly 50 includes the head 37 which pivotally retains a blade holder 56 via an angulation system controlled by a set screw 67, the head 37 holding a blade 60*b*. The blade assembly 52 includes the head 43 which pivotally retains a blade holder 58 via an angulation system controlled by a set screw 68, the head 43 holding a blade 60*c*. The blades 60*a*, 60*b* and 60*c* are preferably, and as shown, identical. While each blade assembly 48, 50, 52 is identical, one or more blade assembly may be different as desired. However, in the preferred embodiment as shown, the three blade assemblies forming a triangular blade assemblage, are identical and fashioned in accordance with the present principles. Therefore, description of one blade assembly of the blade assemblies 48, 50, 52 describes the others of the blade assemblies 48, 50, 52. Moreover, the description of one blade 60*a*, 60*b*, 60*c* of the blade assemblies 48, 50, 52 describes the others of the blades 60*a*, 60*b*, 60*c*. In general, the blade assemblies 48, 50, 52 are each designed for up/down or posterior/anterior translation or angulation. In FIGS. 1, 2 and 4, the blade assemblies 48, 50, 52 are in a 0° or non-angulated position as well as in an un-retracted position. In FIG. 3, the blade assemblies 48, 50, 52 are in a downwardly angled position (an angle downwardly from 0°) as well as in a retracted position.

Figure 5:
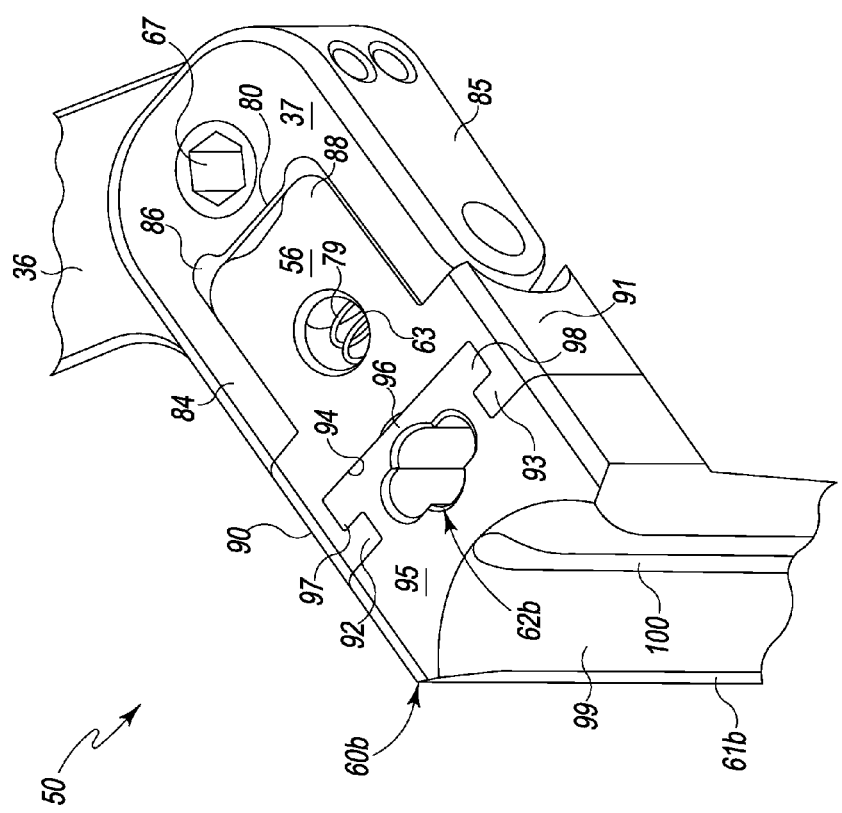
FIG. 5 is an enlarged topside view of a blade assembly on an arm of the spinal retractor of FIG. 1.

With particular reference to FIG. 5 the details of a blade assembly and blade will be described with reference to blade assembly 50. As seen, the blade holder 56 is shown in a 0° position wherein the blade 60*b* is in a full upright or vertical position. The blade holder 56 is pivotally coupled to the head 37. Particularly, an end or tongue 88 of the blade holder 56 is received within a cutout 86 of the head 37 and pivotally connected at sides thereof to arms 84 and 85 of the head 37. This allows the blade holder 56 to pivot relative to the head 37. The blade holder 56 and the head 37 are connected via the angulation adjustment system 63 which includes a worm gear system driven by the hex nut 67. Particularly (and in conjunction with FIG. 3) the hex nut 67 is externally threaded to mesh with screw serrations 80 on an end of the blade holder 56. As the hex nut 67 is rotated clockwise or counterclockwise the blade holder 56 will angulate or pivot up and down. As the blade holder 56 angulates or pivots downward, the spade portion 61*b* of the blade 60*b* moves outwardly (medially or laterally) to effect splaying of the tissue. As seen in FIG. 3, the blade holder 58 includes screw serrations 82 on an end thereof as part of its angulation adjustment system 59.

The blade holder 56 has first and second side arms 90, 91 that define a configured notch 94 that is adapted to receive a configured flange 96 of a head 95 of the blade 60*b*. The blade holder 56 and the blade 60*b* are configured to allow the blade 60*b* to be positively received and held, removed and replaced. Inwardly projecting ends 92, 93 of the first and second side arms 90, 91 define a confined slot for receipt and retention of the blade head 96, the blade flange 96 having lips 97, 98 for complementary reception by the ends 92, 93. The blade 60*b* is thus vertically inserted into and removed from the blade holder 56.

The blade holder 56 incorporates a spring loaded detent system 79 which releasably locks the blade 60*b* into the blade holder 56. The blade 60*b* has a keyed access point 62*b* to allow both insertion of the blade 60*b* into the blade holder 56 as well as actuation of the detent system 79 in order to release the blade 60*b* from the blade holder 56.

The blade 60*b* has a tong, spade, paddle or the like 61*b* that extends transverse from the head 95. An inner surface 99 of the paddle 61*b* is curved inwardly (i.e. concave relative to the head 95). A channel 100 extends from a top of the paddle 61*b* (i.e. the top of the concavity 99) to an end of the paddle 61*b*. The channel 100 receives a shaft that permits anatomical docking of the blade to bony anatomy and/or a cannula in which lighting may be inserted to aid in intraoperative visualization. Rounded corners permit the finestra formed by the blades 60*a*, 60*b*, 60*c* to maintain the same diameter as the blades are angulated.

It should be appreciated that the present spinal retractor 10 provides a table mount connection to secure retractor position relative to the patient via the frame (table). The cephalad/caudal translating arms incrementally lock positions via ratcheting teeth within each ratchet housing and subsequently expand both soft tissue retraction by means of the blades. Each translating arm can be moved independently. The cephalad/caudal translating arms cooperate and co-act with the medial/lateral translating arm to provide a stable finestra and retraction. Thumb actuated depressors release the locked positions of the arms and thus the blades. Adjustable convergence of each translating arm 14, 16, 18 with respective blades creates an adjustable finestra to the surgical site.

Referring now to FIGS. 6-21C, a spinal retractor assembly 210 is shown according to one embodiment. As discussed in greater detail below, retractor assembly 210 may share various functional and structural features with spinal retractor 10. In one embodiment, retractor assembly 210 includes a frame or base 212 (e.g., a plate, frame, or base assembly, etc.), a first side assembly 214, a second side assembly 216, and a center assembly 218. Assemblies 214, 216, and 218 are coupled to base 212 to enable translating movement of assemblies 214, 216, 218 relative to base 212 to provide retraction of tissue, etc. during surgical procedures involving the spine, etc. First and second side assemblies 214, 216 translate relative to frame 212 in a medial-lateral direction (e.g., along a first axis or direction), and center assembly 218 translates relative to frame 212 in a cephalad-caudal direction (e.g., along a second axis or direction) in a generally perpendicular fashion relative to first and second assemblies 214, 216. In one embodiment, each of assemblies 214, 216, 218 may be adjusted (e.g., translated) relative to frame 212 independently (e.g., such that each of assembly 214, assembly 216, and assembly 218 may be adjusted individually).

Figure 6:
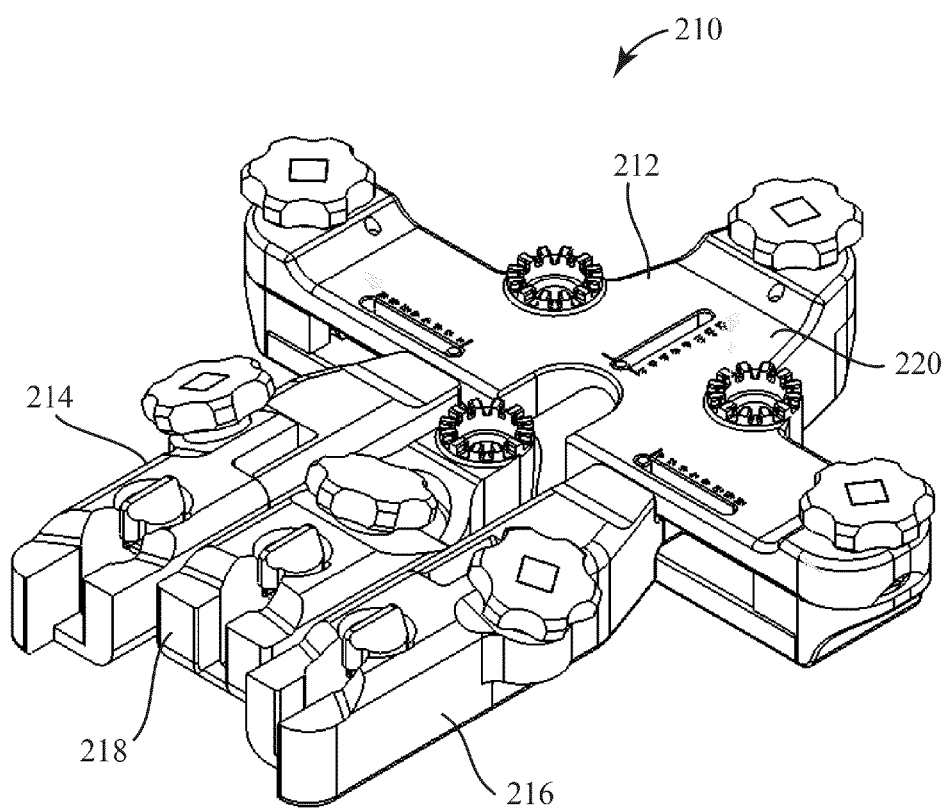
FIG. 6 is a perspective view of a spinal retractor according to an alternative embodiment.
Figure 10:
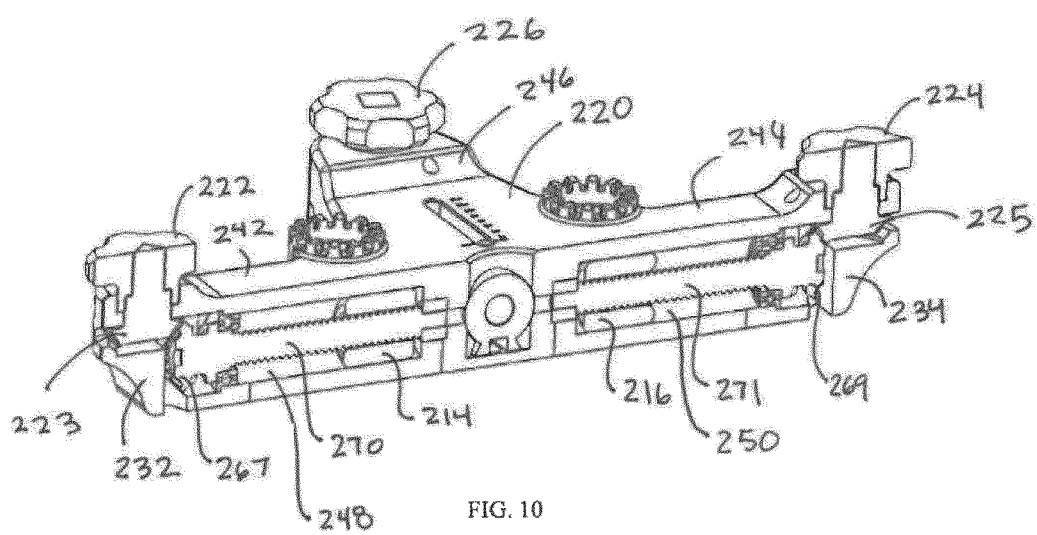
FIG. 10 is a cross-sectional perspective view taken along line 10-10 of FIG. 7 according to one embodiment.

Referring to FIGS. 6 and 10, frame 212 includes body 220, a first side adjustment member or knob 222, a second side adjustment member or knob 224, and a center adjustment member or knob 226. Knobs 222, 224 are coupled to drive members 223, 225, respectively, such that rotation of knobs 222, 224, causes a corresponding rotation of drive members 223, 225. Drive members 223, 225 include bevel gears in one embodiment and, as discussed in greater detail below, are configured to engage bevel gears on corresponding adjustment members. Knob 226 may be coupled to a drive member of similar structure and function.

Figure 7:
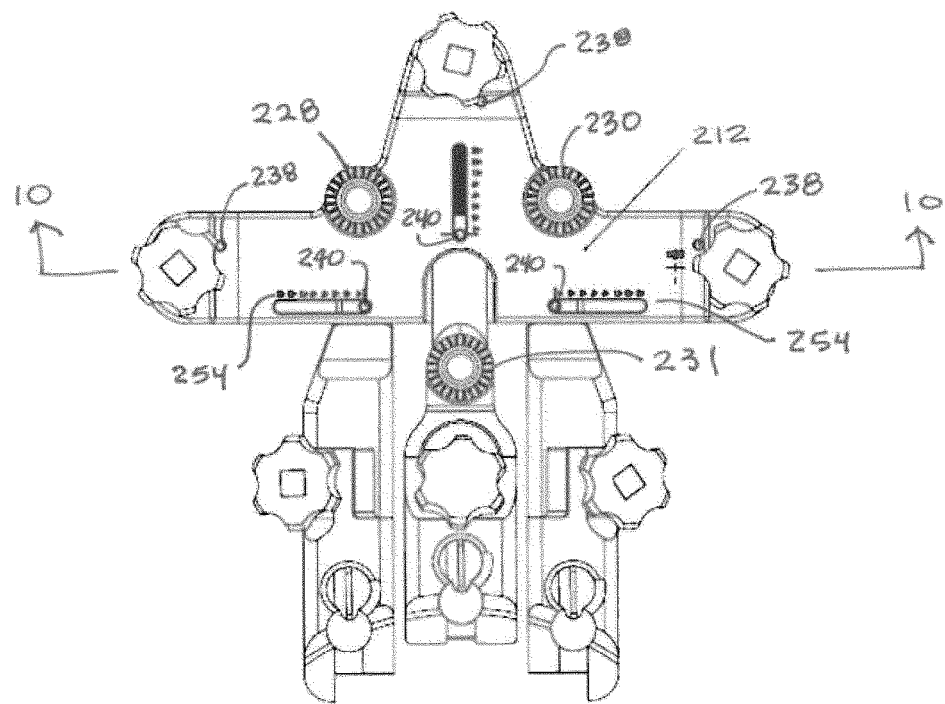
FIG. 7 is a top view of the spinal retractor assembly of FIG. 6 according to one embodiment.
Figure 8:
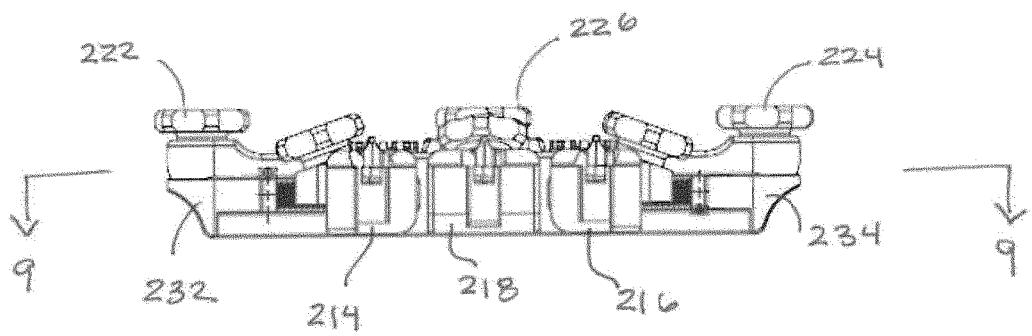
FIG. 8 is a front view of the spinal retractor assembly of FIG. 6 according to one embodiment.

In one embodiment, frame 212 further includes table arm mounts 228, 230, 231 (see FIG. 7). Mounts 228, 230, 231 are configured to enable attachment of refractor assembly 210 to a table arm in a fixed relationship. As such, retractor assembly 210 may be fixed in space via one or both of table mounts 228, 230, 231. Mounts 228, 230, 231 may be located in any suitable locations, and more or fewer mounts may be provided than illustrated according to various alternative embodiments.

Figure 9:
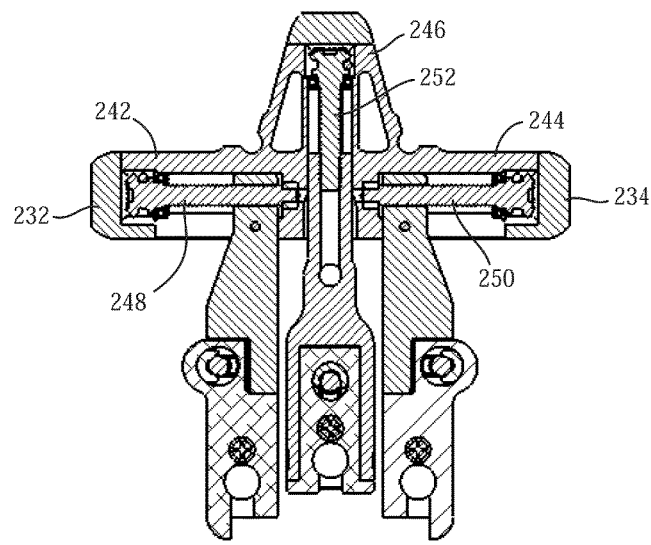
FIG. 9 is a cross-sectional view taken along line 9-9 of FIG. 8 according to one embodiment.
Figure 14:
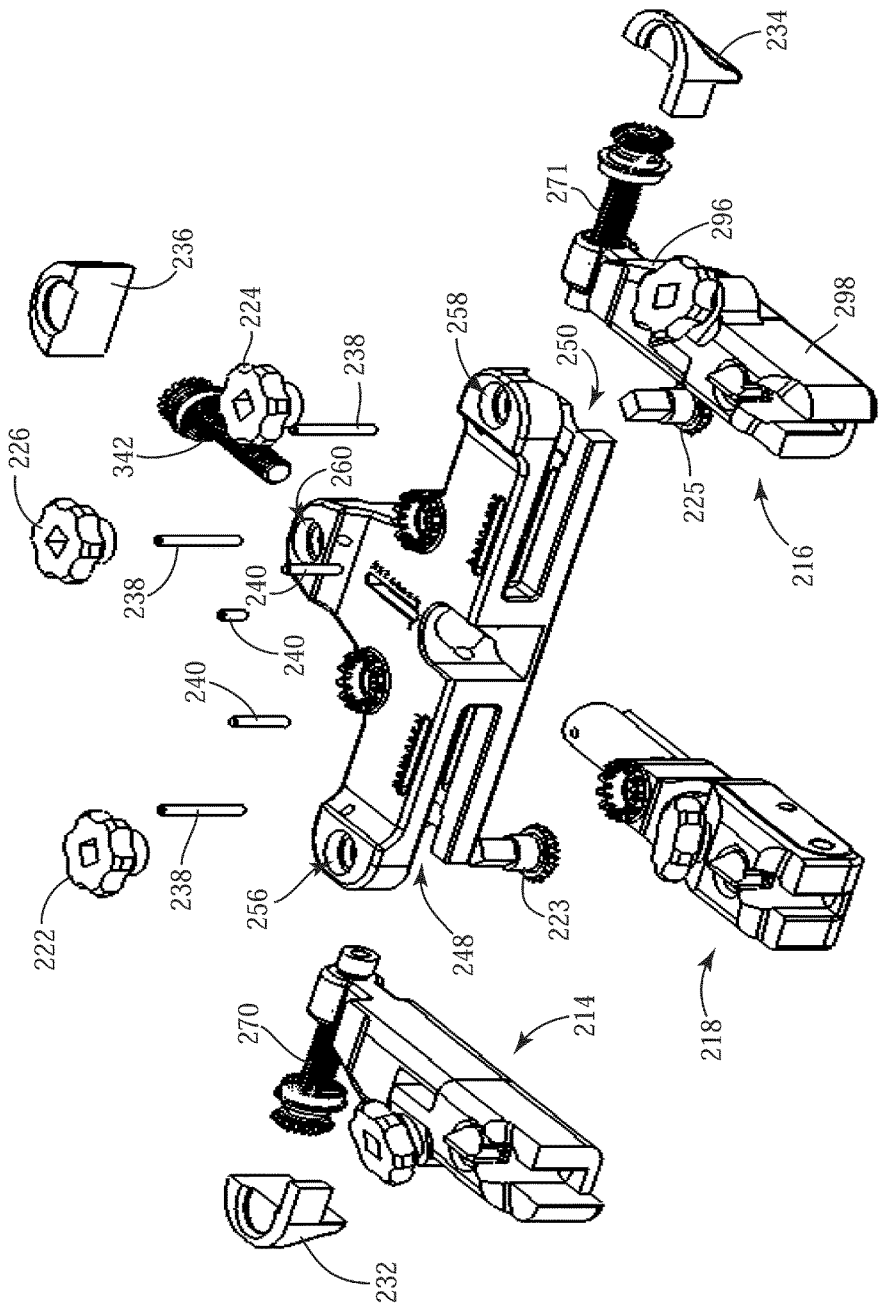
FIG. 14 is an exploded view of the spinal retractor of FIG. 6 according to one embodiment.

Referring FIGS. 9-10 and 14, in some embodiments frame 212 includes first and second side retainers 232, 234. Side retainers are positioned at the lateral ends of frame 212 and form at least a portion of the channels within which assemblies 214, 216 translate. In one embodiment, retainers 232, 234 define a limit to the range of motion of first and second side assemblies 214, 216. Retainers 232, 234 may be coupled to body 220 using any suitable fastening technique, including welding, press fits, mechanical fasteners, and the like. As shown in FIG. 14, a center retainer 236 similarly is coupled to a center portion of body 220 using any suitable fastening technique, including welding, press fits, mechanical fasteners, and the like.

In some embodiments, retaining pins 238 extend through body 220 and, as discussed in greater detail below, are received within annular grooves in threaded members to hold the threaded members in position during use of retractor assembly 210. In one embodiment, three retaining pins 238 are utilized. In other embodiments, more or fewer retaining pins may be used. Further, marker pins 240 may be used in connection with each of first side assembly 214, second side assembly 216, and center assembly 218. Marker pins 240 extend up from assemblies 214, 216, and 218 and through body 220 to provide an indication of the positions of assemblies 214, 216, and 218 relative to body 220, thereby providing a user of retractor assembly 210 a visual indication of the amount of retraction being provided by each of assemblies 214, 216, and 218. In one embodiment, body 220 includes marking gauges 254 (see FIG. 7) having incremental distance markings to provide further information regarding amounts of retraction. Thus, the amount of retraction is indicated by the position of the marking pins 240 along marking gauges 254.

In one embodiment, body 220 includes a first lateral extension 242, a second lateral extension 244, and a central extension 246 (see FIG. 9). First and second lateral extensions 242, 244 generally extend along a common first axis, and central extension 246 generally extends along a second axis perpendicular to the first axis. Central extension 246 is in one embodiment positioned at approximately the midpoint between the opposite ends of first and second lateral extensions 242, 244. A first lateral channel 248 is formed in first lateral extension 242, a second lateral channel 250 is formed in second lateral extension 244, and a central channel or bore 252 is formed in central extension 246. Channels 248, 250, 252 receive end portions of first side assembly 214, second side assembly 216, and center assembly 218, respectively. A first side adjustment aperture 256 is provided on first lateral extension 242, a second side adjustment aperture 258 is provided in second lateral extension 244, and a center adjustment aperture 260 is provided in center extension 246. Adjustment apertures 256, 258, 260 are configured to receive adjustment knobs and/or drive members to enable user-adjustment of first side assembly 214, second side assembly 216, and center assembly 218 relative to body 220.

Referring to FIG. 10, translation of first and second side assemblies 214, 216 is accomplished via rotation of adjustment knobs 222, 224. Adjustment knobs 222, 224 are coupled to drive members 223, 225, which may include bevel gears. Drive members 223, 225 in turn engage bevel gears 267, 269 provided on opposing ends of threaded adjustment members 270, 271, such that rotation of knobs 222, 224 causes a corresponding rotation of adjustment members 270, 271. First and second side assemblies 214, 216 are threadingly received by adjustment members 270, 271 such that rotation of adjustment members 270, 271 causes translation of first and second side assemblies 214, 216. Central assembly is movable in a similar fashion, through use of adjustment knob 226 and adjustment member 342. As such, through selective rotation of knobs 222, 224, and 226, first and second side assemblies 214, 216 and central assembly 218 may be translated independently from one another relative to body or frame 212.

Figure 11:
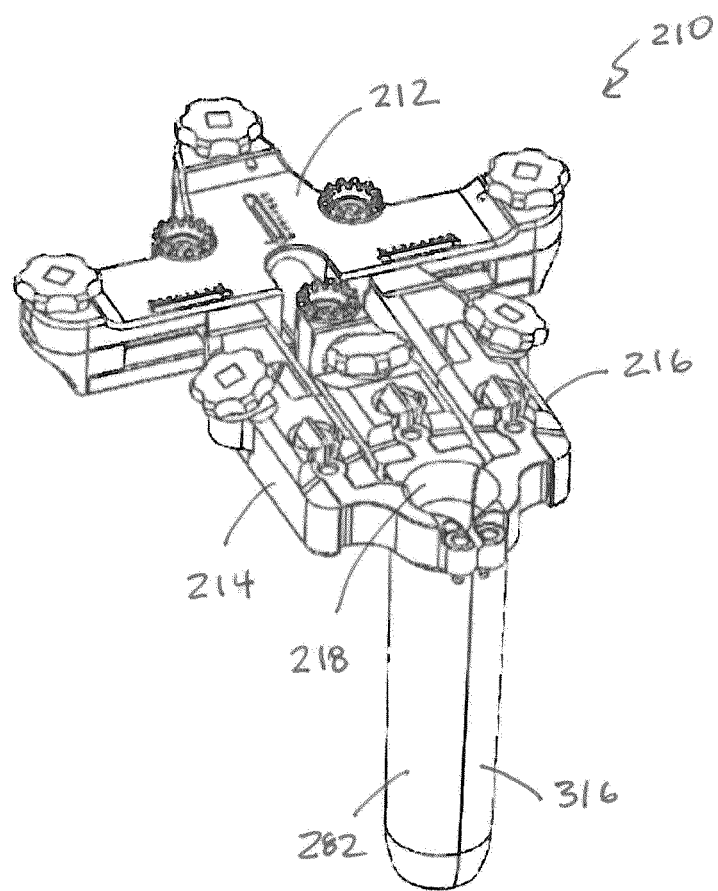
FIG. 11 is a perspective view of a spinal retractor in a closed configuration according to one embodiment.
Figure 12:
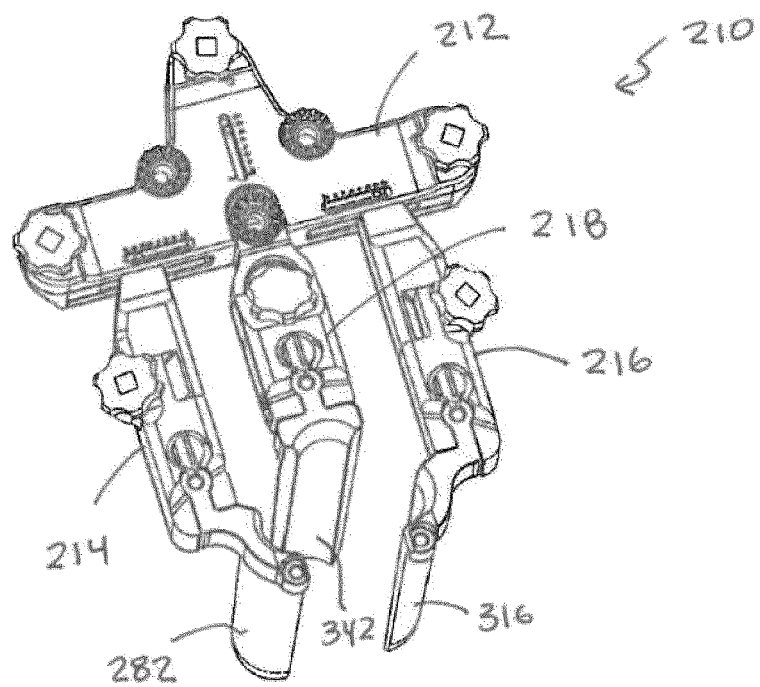
FIG. 12 is a perspective view of the spinal retractor of FIG. 11 in an open configuration according to one embodiment.
Figure 13:
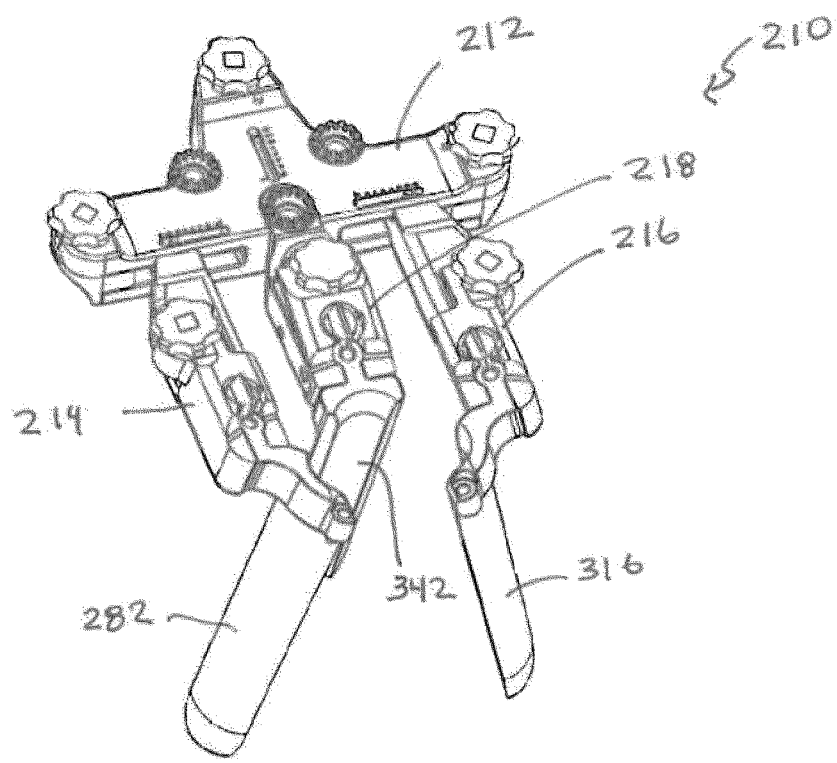
FIG. 13 is a perspective view of the spinal retractor of FIG. 11 in an open configuration with angulated blades according to one embodiment.

Referring to FIGS. 11-13, assembly 210 is movable between a closed configuration, shown in FIG. 11, to an open configuration, shown in FIG. 12, through translation of first and second side assemblies 214, 216 and/or central assembly 218 relative to body 220. Furthermore, first and second side assemblies 214, 216 and central assembly 218 receive blade assemblies 282, 316, and 348, respectively, which are configured to hold tissue apart during various procedures. As shown in FIGS. 12 and 14 and as discussed in greater detail below, blade assemblies 282, 316, 342 may be angulated (e.g., moved from a generally vertical orientation to one or more non-vertical, or angled, orientations) to suit a particular procedure.

Figure 15A:
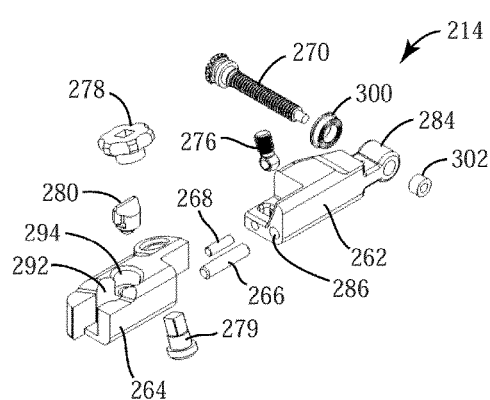
FIGS. 15A-15B illustrate a side assembly of a spinal retractor according to one embodiment.
Figure 15B:
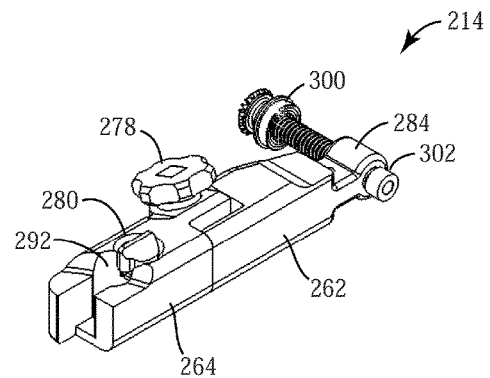

Referring now to FIGS. 15A-15B, first side assembly 214 is shown in greater detail according to one embodiment. Assembly 214 includes a first arm portion 262 coupled to a second arm portion 264. First arm portion 262 and second arm portion 264 can take any suitable size and/or shape, and be coupled together using a variety of coupling methods.

In one embodiment, first arm portion 262 is translatable relative to frame 212, but rotatably fixed relative to frame 212, and second arm portion 264 is rotatably coupled to first arm portion 262. As shown in FIGS. 18A-19B, second arm portion rotates relative to first arm portion 262 about a first pivot pin 266. An adjustment knob 278 is coupled to an insert 279 which threadingly engages an angulation adjustment member 276. Member 276 includes a threaded shaft and rotates about a second pivot pin 268. As shown in FIGS. 18A-19B, as a user turns knob 278, the angular position of second arm portion 264 relative to first arm portion 262 changes due to the travel of insert 279 along member 276, providing angular adjustability of the associated blade assemblies. For example, as shown in FIGS. 18A-B, first and second arm portions 262, 264 are generally aligned, and knob 278 is in a first position. Upon turning knob 278, knob 278 moves to a second position, shown in FIGS. 19A-B, and second arm portion 264 moves to an angulated position with respect to first arm portion 262, thereby enabling additional retraction of surrounding tissue, etc.

Referring to FIG. 15A, first arm portion 262 includes an internally threaded cylindrical portion 284. Portion 284 is received within channel 248 and translates therein. In some embodiments, the outer contour of portion 284 generally corresponds in shape to the inner contour of channel 248 such that portion 284 is limited to translational movement within channel 248. In one embodiment, portion 284 is received within bushings 300, 302, which are provided on threaded member 270 and may act to enable rotation of threaded member 270 within channel 248 and/or define the range of motion of portion 284. First arm portion 262 further includes pin apertures 286, which are sized and shaped to receive first and second pivot pins 266, 268. In order to provide the angulation of second arm portion 264, first arm portion 262 further includes an adjustment surface 288. As shown in FIGS. 18A and 19A, adjustment surface 288 in one embodiment limits the total amount of angulation of second arm portion 264 relative to first arm portion 262.

Second arm portion 264 includes a blade receiving portion 292 and a blade lock bore 294. Blade receiving portion 292 is configured to receive first side blade assembly 282, and blade lock bore 294 is configured to receive blade lock 280. In one embodiment, blade lock 280 includes a non-circular head such that blade lock 280 is rotatable within blade lock bore 294 into and out of an interfering position relative to first side blade assembly 282 when first side blade assembly 282 is received within blade receiving portion 292. As such, first side blade assembly 282 may be slidingly received within blade receiving portion 292 and subsequently maintained in position relative to second arm portion 264 by way of blade lock 280.

Second side assembly 216 in one embodiment operates in a similar manner to first side assembly 214, and includes similar components, including a first arm portion 296 and a second arm portion 298, which receives second blade assembly 316.

Figure 16A:
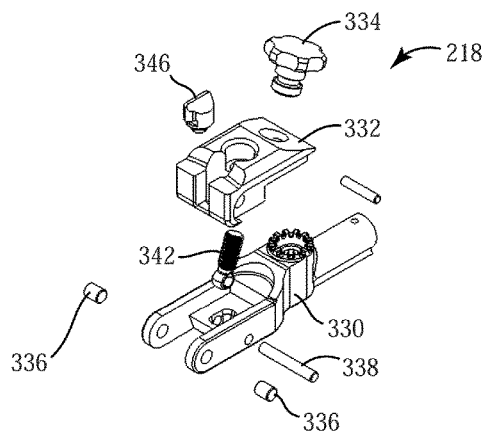
FIGS. 16-16B illustrate a central assembly of a spinal refractor according to one embodiment.
Figure 16B:
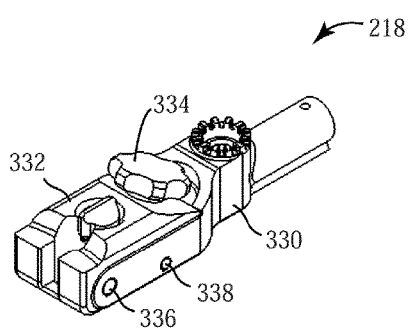

Referring to FIGS. 16A-16B, center assembly 218 includes a first arm portion 330 and second arm portion 332 pivotally coupled to first arm portion 330 via pivot pins 336. An angulation knob 334 threadingly engages an adjustment member 342 to cause rotation of adjustment member 342 about angulation pivot pin 338. Center blade assembly 342 is received by second arm portion 332 and retained in place by a blade lock 346. Rotation of adjustment knob 344 causes a corresponding change in the angulation of center blade assembly 342.

Figure 17:
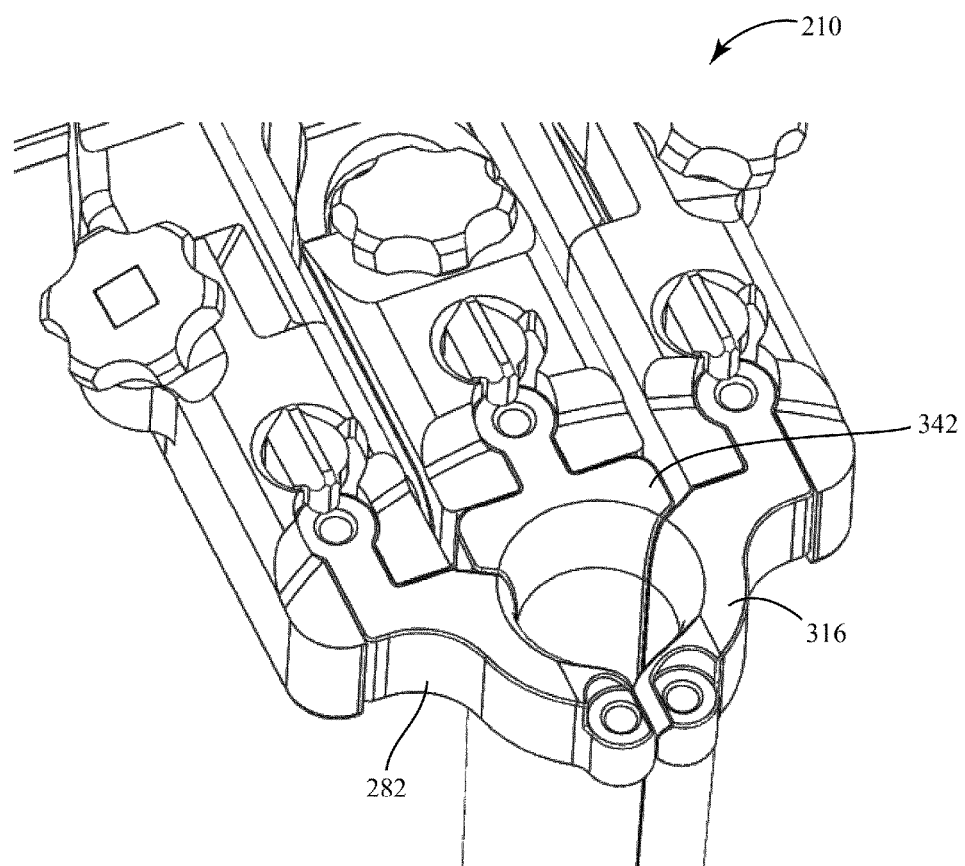
FIG. 17 is a perspective view of a portion of a spinal retractor according to one embodiment.
Figure 20A:
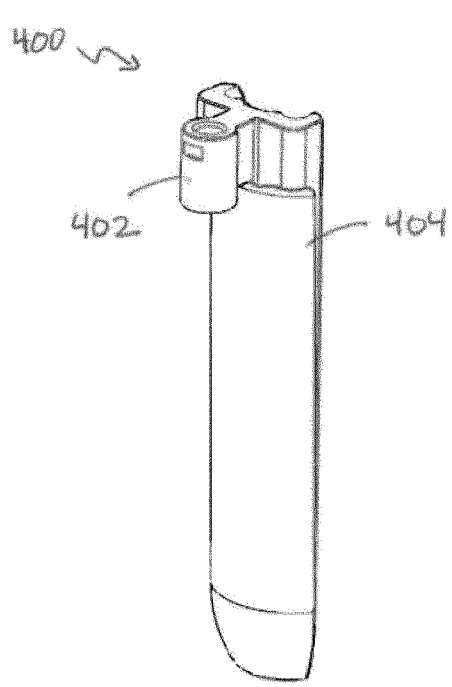
FIGS. 20A-21C illustrate a blade for a spinal retractor according to one embodiment.
Figure 20B:
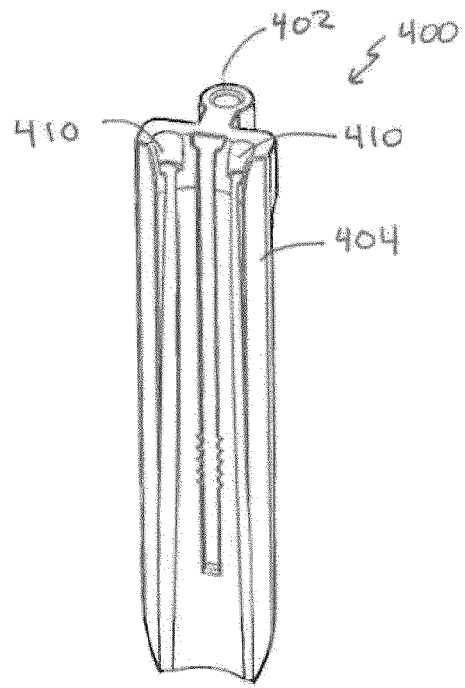
Figure 21A:
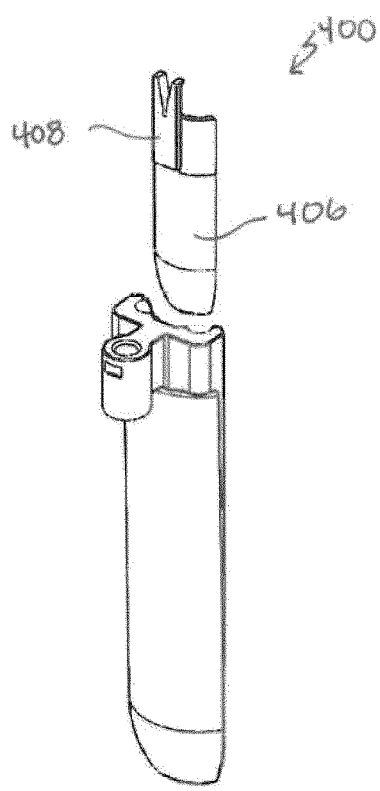
Figure 21B:
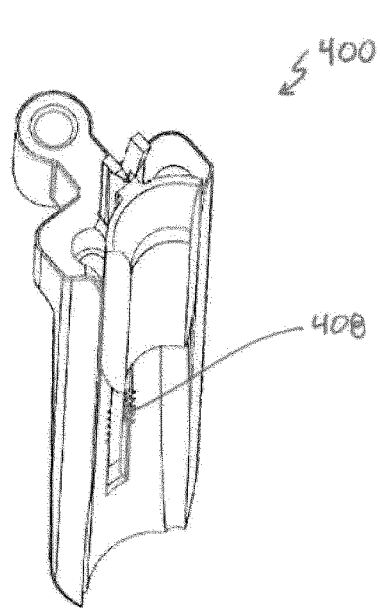
Figure 21C:
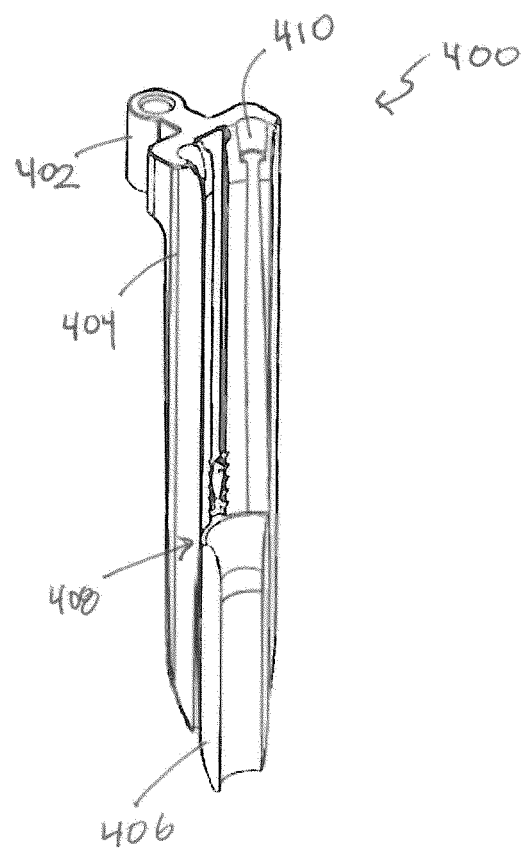

Referring now to FIG. 17, in one embodiment, blade assemblies 282, 316, 342 form a circular interior when spinal retractor 210 is in the closed position and blade assemblies 282, 316, and 342 are in a non-angulated orientation. Dependent upon a desired type and degree of distraction, the various side and center assemblies and blade assemblies may be moved to desired positions to provide the desired retraction for a particular procedure.

Referring to FIGS. 20A-21C, a blade assembly 400 is shown according to an alternative embodiment. The features of blade assembly 400 may be implemented with any of blade assemblies 282, 316, and 342. In one embodiment, blade assembly 400 includes a blade support 402 coupled to a primary blade 404. A secondary blade 406 is removably and adjustably coupled to primary blade 404 via a ratchet mechanism 408. One or more channels 410 may be provided in primary blade 404 to enable insertion of light sources, fixation pins, or other components. For example, in some embodiments, upon positioning blade assembly 400 in a desired retraction position, one or more fixation pins may be placed within channel 410 to secure the blade(s) in place. Use of secondary blade 406 is in some embodiments optional, and enables, for example, prevention of tissue creep during procedures and eliminated the need to change to a longer blade during a procedure.

In use, spinal retractor 210 is positioned at a desired position relative to a patient, and may be secured using one or more of table arm mounts 228, 230, 231. Spinal retractor 210 is normally initially in a closed configuration (see, e.g., FIG. 11). Spinal retractor may be moved to a desired open configuration by translating one or more of first side assembly 214, second side assembly 216, and center assembly 218 relative to base 212. Further, one or more of blade assemblies 282, 316, or 342 (or similarly, blade assembly 400), may be angulated into a desired position of angulation. In some embodiments, a secondary blade may be utilized to prevent tissue creep during a procedure, and one or more components (e.g., lights, fixation pins, etc.) may be utilized via one or more of the blade assemblies.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A retractor assembly, comprising:
a base including:
a body;
first and second threaded shafts provided within the body and extending along a first direction; and
a third threaded shaft provided within the body and extending along a second direction different from the first direction;
a first side arm assembly coupled to a first side of the base and configured to translate relative to the base along the first threaded shaft and along the first direction, wherein the first side arm assembly includes a first arm portion coupled to the first threaded shaft and rotatably fixed relative to the body, and a second arm portion rotatably coupled to the first arm portion, wherein the first and second arm portions of the first side arm assembly extend along and define a first axis extending perpendicular to the first direction and wherein the second arm portion of the first side arm assembly rotates about the first axis relative to the first arm portion of the first side arm assembly and the body;
a second side arm assembly coupled to a second side of the base and configured to translate relative to the base along the second threaded shaft and along the first direction independent from the first side arm assembly, wherein the second side arm assembly includes a first arm portion coupled to the second threaded shaft and rotatably fixed relative to the body, and a second arm portion rotatably coupled to the first arm portion, wherein the first and second arm portions of the second side arm assembly extend along and define a second axis extending perpendicular to the first direction, and wherein the second arm portion of the second side arm assembly rotates about the second axis relative to the first arm portion of the second side arm assembly and the body; and a central arm assembly coupled to the third threaded shaft provided within a center portion of the base and configured to translate relative to the base along the third threaded shaft and along the second direction;

a first adjustment knob operatively coupled to a first knob bevel gear;

a second adjustment knob operatively coupled to a second knob bevel clear;

a third adjustment knob coupled to a third knob bevel gear;

wherein the first threaded shaft is operatively coupled to a first shaft bevel gear, and wherein the first knob bevel gear engages the first shaft bevel gear such that rotation of the first adjustment knob causes translation of the first side arm assembly along the first threaded shaft; and wherein the second threaded shaft is operatively coupled to a second shaft bevel gear, and wherein the second knob bevel gear engages the second shaft bevel gear such that rotation of the second adjustment knob causes translation of the second side arm assembly along the second threaded shaft;

wherein the third threaded shaft is operatively coupled to a third shaft bevel gear, and wherein the third knob bevel gear engages the third shaft bevel gear such that rotation of the third adjustment knob causes translation of the central arm assembly along the third threaded shaft;

wherein the first threaded shaft, the second threaded shaft, and the third threaded shaft all lie within the body and extend in a common plane when provided within the body of the base.

2. The retractor assembly of claim 1, wherein each of the first threaded shaft, the second threaded shaft, and the third threaded shaft is rotatable relative to the body and translationally fixed relative to the body.

3. The retractor assembly of claim 1, wherein the second arm portion of the first side arm assembly and the second arm portion of the second side arm assembly each include a blade assembly configured to retract tissue.

4. The retractor assembly of claim 1, wherein the first arm portion of the first side arm assembly and the first arm portion of the second side arm assembly each includes a marking pin extending through a portion of the body to provide an indication of the positions of the first side arm assembly and the second side arm assembly relative to the base.

5. A retractor assembly, comprising:
a base;
a first threaded shaft disposed in the base and extends along a first direction:
a second threaded shaft disposed in the base and extends along the first direction:
a central threaded shaft disposed in the base and extends along a second direction different from the first direction;
a first side arm assembly coupled to a first side of the base and configured to translate relative to the base along the first threaded shaft disposed in the base and along a first direction, wherein the first side arm assembly includes a first arm portion coupled to the first threaded shaft, and a second arm portion rotatably coupled to the first arm portion, wherein the first and second arm portions of the first side arm assembly extend along and define a first axis extending perpendicular to the first direction and wherein the second arm portion of the first side arm assembly rotates about the first axis relative to the first arm portion of the first side arm assembly and the base;

a second side arm assembly coupled to a second side of the base and configured to translate relative to the base along the second threaded shaft disposed within the base and along the first direction independent from the first side arm assembly, wherein the second side arm assembly includes a first arm portion coupled to the second threaded shaft, and a second arm portion rotatably coupled to the first arm portion, wherein the first and second arm portions of the second side arm assembly extend along and define a second axis extending perpendicular to the first direction and wherein the second arm portion of the second side arm assembly rotates about the second axis relative to the second arm portion of the second side arm assembly and the base; and a central arm assembly coupled to a center portion of the base and configured to translate relative to the base along the central threaded shaft disposed in the base and along the second direction;

wherein the first threaded shaft is operatively coupled to a first shaft bevel gear, wherein the first shaft bevel gear engages a first knob bevel gear, and wherein the first knob bevel gear is operatively coupled to a first adjustment knob such that rotation of the first adjustment knob causes translation of the first side arm assembly along the first threaded shaft;

wherein the second threaded shaft is operatively coupled to a second shaft bevel gear, wherein the second shaft bevel gear engages a second knob bevel gear, and wherein the second knob bevel gear is operatively coupled to a second adjustment knob such that rotation of the second adjustment knob causes translation of the second side arm assembly along the second threaded shaft;

wherein the central threaded shaft is operatively coupled to a third shaft bevel gear, wherein the third shaft bevel gear engages a third knob bevel gear, and wherein the third knob bevel gear is operatively coupled to a third adjustment knob such that rotation of the third adjustment knob causes translation of the central arm assembly along the central threaded shaft;

wherein the first threaded shaft, the second threaded shaft, and the central threaded shaft extend in a common plane when disposed in the base.

6. The retractor assembly of claim 5, wherein each of the first threaded shaft, the second threaded shaft, and the central threaded shaft is rotatable relative to the base and translationally fixed relative to the base.

7. The retractor assembly of claim 5, wherein the second arm portion of the first side arm assembly and the second arm portion of the second side arm assembly each include a blade assembly configured to retract tissue.

8. The retractor assembly of claim 7, wherein the first arm portion of the first side arm assembly and the first arm portion of the second side arm assembly each includes a marking pin extending through a portion of the body to provide an indication of the position of the first side arm assembly and the second side arm assembly relative to the body.

9. The retractor assembly of claim 7, wherein the blade assembly includes a primary blade and secondary blade removably coupled to the primary blade.

* * * * *